United States Patent [19]

Lesson et al.

[11] Patent Number: 5,670,522

[45] Date of Patent: Sep. 23, 1997

[54] DOPAMINE RECEPTOR SUBTYPE LIGANDS

[75] Inventors: Paul David Lesson, Cambridge; Michael Rowley, Harlow, both of United Kingdom

[73] Assignee: Merck Sharp & Dohme Limited, Hoddesdon, England

[21] Appl. No.: 424,289

[22] PCT Filed: Oct. 22, 1993

[86] PCT No.: PCT/GB93/02189

§ 371 Date: Apr. 20, 1995

§ 102(e) Date: Apr. 20, 1995

[87] PCT Pub. No.: WO94/10162

PCT Pub. Date: May 11, 1994

[30] Foreign Application Priority Data

Oct. 23, 1992 [GB] United Kingdom ............. 9222264
Oct. 23, 1992 [GB] United Kingdom ............. 9222266

[51] Int. Cl.⁶ .................. A61K 31/445; A61K 31/41; C07D 401/04; C07D 413/04
[52] U.S. Cl. .................. 514/322; 514/321; 514/379; 514/403; 546/198; 546/199; 546/225; 548/241; 548/359.1
[58] Field of Search .................. 514/321, 379, 514/322, 403; 546/198, 199, 225; 548/241, 359.1

[56] References Cited

U.S. PATENT DOCUMENTS

| | | | |
|---|---|---|---|
| 3,926,988 | 12/1975 | Krapcho et al. | 544/140 |
| 3,932,430 | 1/1976 | Habeck | 546/275.7 |
| 3,940,418 | 2/1976 | Hamilton | 548/359.1 |
| 3,957,816 | 5/1976 | Habeck | 548/359.1 |
| 3,959,308 | 5/1976 | Coombs | 548/359.1 |
| 4,173,634 | 11/1979 | Krapcho | 514/232.8 |

FOREIGN PATENT DOCUMENTS 2119977 12/1971 Germany.

OTHER PUBLICATIONS

AMA Abstract "Analysis of the D4/dopamine receptor gene variant in an Italian schizophrenia kindred" AMA Apr. 1994, p. 288 1994.

Primary Examiner—Ceila Chang
Attorney, Agent, or Firm—Mary A. Appollina; Melvin Winokur

[57] ABSTRACT

Fused tricyclic heteroaromatic compounds of formula

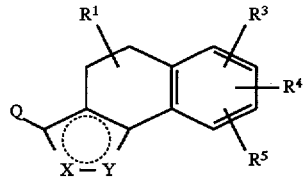

wherein one of X and Y represents nitrogen, and the other of X and Y represents oxygen, sulphur or N—$R^2$;

Q represents a substituted five- or six-membered monocyclic heteroaliphatic ring which contains one nitrogen atom as the sole heteroatom and is linked to the five-membered heteroatomic ring containing the moieties X and Y via a carbon atom: as well as substituted 3,4-dihydro-1-hydroxy-2-oxomethyl-naphthalene precursors thereto, are ligands for dopamine receptor subtypes within the body and are therefore useful in the treatment of disorders of the dopamine system, in particular schizophrenia.

6 Claims, No Drawings

DOPAMINE RECEPTOR SUBTYPE LIGANDS

This application is a 371 of PCT/GB93/02189 filed Oct. 22, 1993.

This invention relates to fused tricyclic heteroaromatic compounds, and to beta-dicarbonyl precursors thereto, which are ligands for dopamine receptor subtypes within the body. More particularly, the invention is concerned with compounds containing an isoxazole, isothiazole or pyrazole ring fused to a dihydronaphthalene moiety, and with substituted 3,4-dihydro-1-hydroxy-2-oxomethyl-naphthalene precursors thereto. Being ligands for dopamine receptor subtypes within the body, the compounds according to the invention are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

In EP-A-0135781 and EP-A-0402644 there is described a class of indazole and related fused bicyclic heteroaromatic derivatives which are alleged to have antipsychotic activity.

The compounds in accordance with the present invention, being ligands for dopamine receptor subtypes within the body, are accordingly of use in the treatment and/or prevention of disorders of the dopamine system.

In one aspect, therefore, the present invention provides a compound of formula I, or a salt thereof or a prodrug thereof:

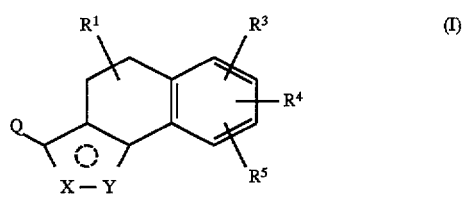

wherein the broken circle represents two non-adjacent double bonds in any position within the five-membered ring;

one of X and Y represents nitrogen, and the other of X and Y represents oxygen, sulphur or N—$R^2$;

Q represents a substituted five- or six-membered monocyclic heteroaliphatic ring which contains one nitrogen atom as the sole heteroatom and is linked to the five-membered heteroatomic ring containing the moieties X and Y via a carbon atom;

$R^1$ and $R^2$ independently represent hydrogen or $C^{1-6}$ alkyl;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, $SO_2R^a$, —$SO_2NR^aR^b$, —$NR^aR^b$, —$NR^aCOR^b$, —$NR^aCO_2R^b$, —$COR^a$, —$CO_2R^a$ or —$CO_2NR^aR^b$; and $R^a$ and $R^b$ independently represent hydrogen, hydrocarbon or a heterocyclic group.

The five-membered heteroaromatic ring containing the moieties X and Y in formula I above may be a substituted isoxazole, isothiazole or pyrazole ring, preferably isoxazole or pyrazole.

The monocyclic heteroaliphatic ring Q in the compounds of formula I above represents a substituted pyrrolidyl or piperidyl moiety linked through carbon. Examples of suitable rings include the moieties of formula Qa to Qe:

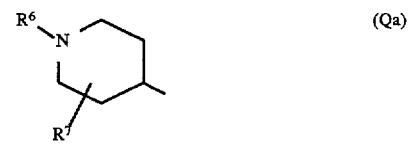

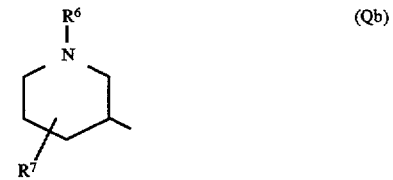

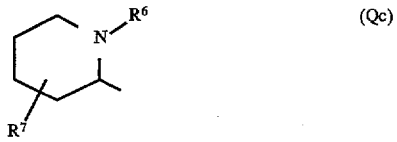

-continued

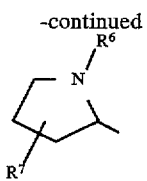

wherein one of $R^6$ and $R^7$ represents hydrocarbon or a heterocyclic group, and the other of $R^6$ and $R^7$ represents hydrogen, hydrocarbon or a heterocyclic group.

Particular monocyclic heteroaliphatic rings represented by the substituent Q in formula I include the rings of structure Qa, Qb and Qd above, especially Qa.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular $C_{3-7}$ cycloalkyl($C_{1-6}$)alkyl groups include cyclopropylmethyl and cyclohexylmethyl.

Particular aryl groups include phenyl, naphthyl and tetrahydronaphthyl.

Particular aryl($C_{1-6}$)alkyl groups include benzyl, naphthylmethyl, phenethyl and phenylpropyl.

Particular aryl($C_{2-6}$)alkenyl groups include phenylethenyl and phenylpropenyl.

A particular aryl($C_{2-6}$)alkynyl group is phenylethynyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, imidazolyl, oxadiazolyl and thiadiazolyl groups.

Particular heteroaryl($C_{1-6}$)alkyl groups include pyridylmethyl, furylmethyl, indolylmethyl, pyrazinylmethyl and pyridylethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R'", —NR'COR'", —NR'CO$_2$R'", —NR'SO$_2$R'", —CH$_2$NR'SO$_2$R'", —NHCONR'R'", —CONR'R'", —SO$_2$NR'R'" and —CH$_2$SO$_2$NR'R'", in which R' and R'" independently represent hydrogen, $C_{1-6}$ alkyl, aryl or aryl($C_{1-6}$)alkyl.

The term "halogen" as used herein includes fluorine, chlorine, bromine and iodine, especially chlorine.

The compounds of formula I above may be prepared by a process which comprises reacting a compound of formula II with a compound of formula III:

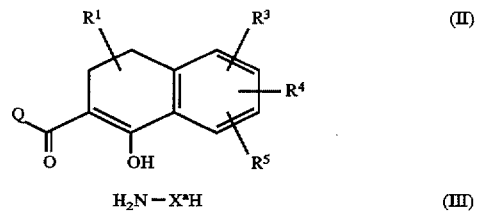

wherein Q, $R^1$, $R^3$, $R^4$ and $R^5$ are as defined above, and $X^a$ represents oxygen, sulphur or N—$R^2$ in which $R^2$ is as defined above; followed, if necessary, by separation of the resulting mixture of isomers by conventional means.

The reaction is conveniently carried out by stirring the reactants in a suitable solvent, for example a mixture of N,N-dimethylformamide and methanol, optionally in the presence of a non-nucleophilic base such as ethyldiisopropylamine, suitably at room temperature. Depending upon the nature of the reactants and of the chosen reaction conditions, the reaction may afford the desired product in a single step, or may proceed via the intermediates IVA and IVB:

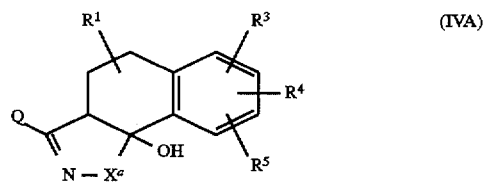

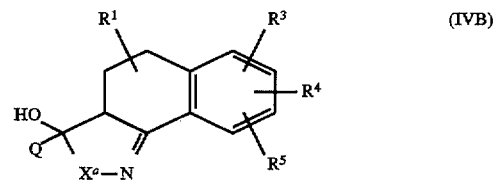

wherein Q, $R^1$, $R^3$, $R^4$, $R^5$ and $X^a$ are as defined above.

The intermediates IVA and IVB can be converted into the corresponding products of formula I by dehydration. This is conveniently effected by converting the hydroxy group into a leaving group, suitably by treatment with methanesulphonyl chloride in dichloromethane at 0° C., and treating the resulting compound, ideally in situ, with a base such as triethylamine.

As indicated above, the overall reaction between compounds II and III will usually give rise to a mixture of isomeric products of formula I, in one of which X represents nitrogen and Y represents oxygen, sulphur or N—$R^2$, and in the other of which the X and Y moieties are reversed. For this reason, it will generally be necessary to separate the mixture of isomers obtained therefrom by conventional methods such as chromatography.

The compounds of formula II above are active in their own right as ligands for dopamine receptor subtypes within the body. These compounds, and salts thereof and prodrugs thereof, accordingly represent a further aspect of the present invention.

As will be appreciated, the compounds of formula II as depicted above will generally exist in equilibrium with their other tautomeric forms, including structures (A) and (B):

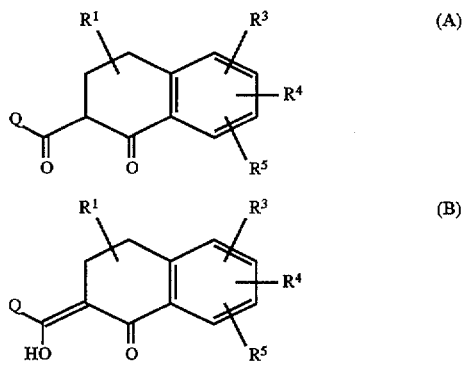

wherein Q, $R^1$, $R^3$, $R^4$ and $R^5$ are as defined above. It is to be understood that all tautomeric forms of the compounds of formula II, as well as all possible mixtures thereof, are included within the scope of the present invention.

For use in medicine, the salts of the compounds of formulae I and II will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formulae I and II above. In general, such prodrugs will be functional derivatives of the compounds of formulae I and II which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituents $R^1$ and $R^2$ independently represent hydrogen or methyl.

Suitable values for the substituents $R^3$, $R^4$ and $R^5$ include hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, nitro, methoxy and chloro.

Suitable values for the substituents $R^6$ and $R^7$ include $C_{1-6}$ alkyl, $C_{2-6}$ alkenyl, $C_{3-7}$ cycloalkyl($C_{1-6}$)alkyl, aryl, aryl($C_{1-6}$)alkyl, aryl($C_{2-6}$)alkenyl and heteroaryl($C_{1-6}$)alkyl, any of which groups may be optionally substituted. In addition, one of $R^6$ and/or $R^7$ may represent hydrogen. Examples of suitable substituents on the groups $R^6$ and/or $R^7$ include $C_{1-6}$ alkyl, halogen, $C_{1-6}$ alkoxy, keto and nitro.

Particular values of $R^6$ and $R^7$ include hydrogen, methyl, allyl, cyclopropylmethyl, cyclohexylmethyl, tetrahydronaphthyl, benzyl, methyl-benzyl, chlorobenzyl, dichlorobenzyl, methoxy-benzyl, nitro-benzyl, naphthylmethyl, phenethyl, methoxy-phenethyl, phenylcarbonylmethyl, phenylpropyl, phenylpropenyl, furylmethyl, indolylmethyl and pyridylethyl, provided that at least one of $R^6$ and $R^7$ is other than hydrogen. Suitably, one of $R^6$ and $R^7$ represents hydrogen, and the other of $R^6$ and $R^7$ is other than hydrogen. Preferably, $R^7$ represents hydrogen and $R^6$ is other than hydrogen, especially benzyl or phenethyl.

A particular sub-class of compounds according to the invention is represented by the compounds of formula IA, and salts and prodrugs thereof:

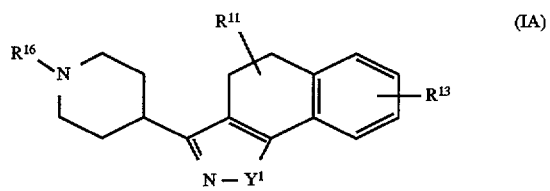

wherein $Y^1$ represents oxygen, sulphur or N—$R^{12}$;

$R^{11}$ and $R^{12}$ independently represent hydrogen or $C_{1-6}$ alkyl;

$R^{13}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{16}$ represents $C_{2-6}$ alkenyl, $C_{3-7}$ cycloalkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted.

Examples of suitable substituents on the group $R^{16}$ include one or more of $C_{1-6}$ alkyl, halogen, $C_{1-6}$ alkoxy, keto and nitro.

Particular values of $R^{16}$ with reference to formula IA above include allyl, cyclopropylmethyl, cyclohexylmethyl, tetrahydronaphthyl, benzyl, methyl-benzyl, chlorobenzyl, dichlorobenzyl, methoxy-benzyl, nitro-benzyl, naphthylmethyl, phenethyl, methoxy-phenethyl, phenylcarbonylmethyl, phenylpropyl, phenylpropenyl, furylmethyl, indolylmethyl and pyridylethyl, especially benzyl or phenethyl.

Particular values of y1 with reference to formula IA above include oxygen or N—$R^{12}$, preferably oxygen, NH or N-methyl and especially NH.

Suitably, $R^{11}$ and $R^{12}$ independently represent hydrogen or methyl, especially hydrogen.

Particular values of $R^{13}$ include hydrogen, methyl, ethyl, isopropyl, nitro, methoxy and chloro, especially hydrogen.

Another sub-class of compounds according to the invention is represented by the compounds of formula IIA, and salts and prodrugs thereof:

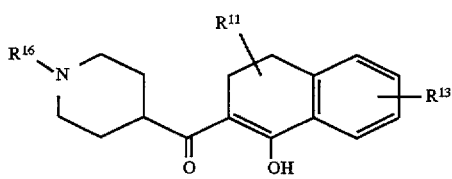

(IIA)

wherein $R^{11}$, $R^{13}$ and $R^{16}$ are as defined with reference to formula IA above.

Specific compounds within the scope of the present invention include:

2-[1-(2-phenylethyl)piperidin-4-ylcarbonyl]-3,4-dihydro-1-hydroxynaphthalene;
2-(1-benzylpiperidin-4-ylcarbonyl)-3,4-dihydro-1-hydroxynaphthalene;
3-(1-benzylpiperidin-4-yl)-4,5-dihydrobenz[g]indazole:
3-[1-(2-phenylethyl)piperidin-4-yl]-4,5-dihydrobenz[g]indazole;
3-[1-(2-phenylethyl)piperidin-4-yl]-4,5-dihydronaphth[1,2-c]isoxazole:
3-[1-(2-phenylethyl)piperidin-4-yl]-4,5-dihydronaphth[2,1-d]isoxazole;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories: for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula II as defined above may be prepared by reacting a carboxylic acid of formula V, or an activated derivative thereof, with two equivalents of a metal enolate of formula VI:

(V)

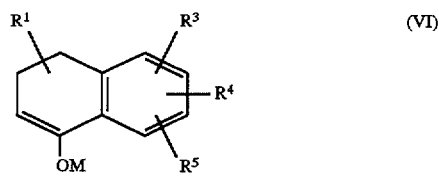

(VI)

wherein $R^1$, $R^3$, $R^4$ and $R^5$ are as defined above, $Q^1$ corresponds to the moiety Q as defined above or represents a precursor thereto protected on the nitrogen atom, and M represents a metal capable of providing a suitable counterion for the enolate anion; followed, where required, by removal of the N-protecting group from the moiety $Q^1$; and subsequently, if necessary, attachment to the nitrogen atom thereby deprotected of an appropriate substituent by standard means to afford a product containing the desired moiety Q.

For example, the substituent $Q^1$ in compound V may represent a moiety of formula Qa to Qe as defined above, in which $R^7$ is hydrogen and $R^6$ represents an N-protecting group. Once the reaction between compounds V and VI is complete, the N-protecting group must be removed, and the desired group $R^6$ subsequently attached, by conventional methods.

The metal M is suitably an alkali metal, especially lithium.

The activated derivative of the carboxylic acid V is suitably the compound formed by reaction between the carboxylic acid V and 1,1'-carbonyldiimidazole, conveniently in tetrahydrofuran at room temperature.

Where the substituent $Q^1$ represents a precursor to the moiety Q protected on the nitrogen atom, the N-protecting group is suitably an alkoxycarbonyl moiety such as t-butoxycarbonyl (BOC), in which case the N-protecting group can conveniently be removed subsequently as necessary by treatment under acidic conditions, e.g. stirring in hydrochloric acid or trifluoroacetic acid.

The reaction between compound V, or the activated derivative thereof, and compound VI is suitably carried out in a solvent such as tetrahydrofuran, commencing at −78° C. with warming to 0° C.

The metal enolate of formula VI is ideally prepared by reacting the corresponding carbonyl compound of formula VII:

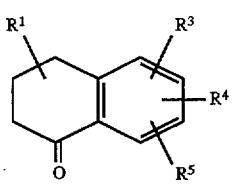

(VII)

wherein $R^1$, $R^3$, $R^4$ and $R^5$ are as defined above; with a non-nucleophilic base such as lithium diisopropylamide, suitably in tetrahydrofuran at −78° C.

Where they are not commercially available, the starting materials of formula III, V and VII may be prepared by standard methods well known from the art.

It will be appreciated that any compound of formula I initially obtained from any of the above processes may, where appropriate, subsequently be elaborated into a further desired compound of formula I using techniques known from the art. For example, the groups $R^2$ and/or $R^6$ may conveniently be attached to a product obtained from any of the above-described processes by means of standard carbon-nitrogen bond-forming reactions well known from the art, such as N-alkylation. By way of illustration, a compound wherein $R^6$ is hydrogen initially obtained may subsequently be N-benzylated by treatment with a benzyl halide, e.g. benzyl bromide, typically under basic conditions, e.g. using triethylamine in a mixture of dichloromethane and N,N-dimethylformamide, suitably at room temperature, to afford a product wherein $R^6$ is benzyl.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM Mg $SO_4$ for 20 min on ice. Membranes were centrifuged at 50,000 g fop 15 min at 4° C. and the resulting pellets resuspended in assay buffer (50 mMTris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 µg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

2-(4-(1-(2-Phenylethyl))piperidinocarbonyl)-3,4-dihydro-1-hydroxynaphthalene

α-Tetralone (6.4g) in THF (15 ml) was added over 5 min to a solution of lithim diisopropylaruide (45 mmol) in THF (150 ml) under nitrogen at −78° C., then stirred for 45 min, to give an orange solution. Carbonyldiimidazole (3.89 g) was added to a solution of N-tert-butyloxycarbonyl isonipecotic acid (5 g) in THF (100 ml) at room temperature under nitrogen, stirred for 45 min, then cannulated into the above orange solution at −78° C. After a further 40 min the mixture was warmed to room temperature, diluted with ethyl acetate, washed with saturated sodium hydrogencarbonate solution, water, and brine, dried ($MgSO_4$) and evaporated in vacuo to give a yellow oil (13.1 g). The oil was dissolved in ethyl acetate (15 ml), then a saturated solution of HCl in ethyl acetate (40 ml) added. When effervescence stopped the mixture was heated to boiling, cooled, and the solid collected, washed with ethyl acetate, and dried to give 3.12 g of an off-white amorphous solid, mp 257°–259° C. 1.12 g of this solid was suspended in dimethylformamide (10 ml) with N-ethyl-N,N-diisopropylamine (1.49 ml) and 2-phenylethyl bromide (0.63 ml), stirred at room temperature for 3 days, then at 70° C. for 17 h. Water (50 ml) was added and the mixture extracted with ethyl acetate (2×30 ml), and the combined organic extracts washed with water, and brine, dried ($MgSO_4$), evaporated in vacuo and purified by flash chromatography, eluting with a gradient of 1% to 5% v/v methanol in dichloromethane containing 1% v/v triethylamine to give the title compound (0.64 g) as off white needles, m.p. 85°–86° C. (from ethanol). (Found: C, 79.93; H, 7.47; N, 4.04. $C_{24}H_{27}NO_2$ requires C, 79.74; H, 7.53; N, 3.87%); δ (360 MHz, $d_6$-DMSO) 1.6–1.8 (4H, m, COCHC $\underline{H}_2$), 2.04 (2H, t, J 11, $CH_2$), 2.5–2.6 (2H, m $CH_2$), 2.62 (2H, t, J 7, $CH_2$), 2.75 (2H, t, J 7, $CH_2$), 2.85 (2H, t, J 7, $CH_2$), 2.9–3.1 (3H, m, $CH_2$ and CH), 7.1–7.5 (8H, m, ArH), 7.81 (1H, d, J 7, naphthalene H-8), 15.2 (1H, br s, OH); small signals can be seen for the keto tautomer; m/z (CI$^+$, $NH_3$) 362 (M$^+$+H).

EXAMPLE 2

2-(4-(1-Benzyl)piperidinocarbonyl)-3,4-dihydro-1-hydroxyn aphthalene: white cubes, mp 99°–101° C. (from ethanol) (Found: C, 78.25; H, 7.30; N, 4.10. $C_{23}H_{25}NO_2$+ 0.3 $H_2O$ requires C, 78.29; H, 7.31; N, 3.97%); δ (360 MHz, $CDCl_3$) 1.7–1.8 (2H, m, $CH_2$), 1.8–1.9 (2H, m, $CH_2$), 2.0–2.1 (2H, m, $CH_2$), 2.62 (3H, t, J 7, one $CH_2$ of ArCH$_2$CH$_2$), 2.6–2.7 (1H, m, CH), 2.85 (2H, t, J 7, other CH$_2$ of ArCH$_2$CH$_2$), 2.98 (2H, d, J 11, NCH$_A$H$_B$CH$_2$), 3.55 (2H, s, ARCH$_2$), 7.1–7.4 (8H, m, ArH), 7.93 (1H, d, J 7, ArH, naphthalene H-8), 15.35 (1H, s, OH); small signals for the keto tautomer can also be seen; m/z (CI$^+$, NH$_3$) 348 (M$^+$+H).

EXAMPLE 3

3-(1-(2-Phenylethyl)-4-piperidinyl)-4,5-dihydrobenz[g]indazole 2-(4-(1-(2-Phenylethyl))piperidinocarbonyl)-3,4-dihydro-1-hydroxynaphthalene (158 mg) was stirred with hydrazine hydrate (50 mg) in methanol (3 ml) under nitrogen for 17 h. The mixture was evaporated in vacuo, dissolved in ethyl acetate, washed with water, and brine, dried (MgSO$_4$), and evaporated in vacuo to give the title compound as white needles.

m.p. 151°–152° C. (from ethanol). (Found: C, 78.77; H, 7.53; N, 11.39. C$_{24}$H$_{27}$N$_3$+0.5 H$_2$O requires C, 78.65; H, 7.70; N, 11.46%); δ (360 MHz, d$_6$-DMSO) 1.7–1.8 (4H, m, CH$_2$'s), 2.0–2.1 (2H, m, CH$_2$), 2.5–2.6 (2H, m, CH$_2$), 2.6–2.7 (3H, m, CH$_2$+CH), 2.75 (2H, t, J 7, CH$_2$), 2.85 (2H, t, J 7, CH$_2$), 3.02 (2H, d, J 11, NCH$_A$H$_B$CH$_2$CH), 7.1–7.3 (8H, m, ArH), 7.6 (1H, br s, ArH), 12.3 (1H, br s, NH); m/z (CI$^+$, NH$_3$) 358 (M$^+$+H).

EXAMPLE 4

3-(1-Benzyl-4-piperidinyl)-4,5-dihydrobenz[g]indazole

Purified by preparative thin layer chromatography, eluting with 3% methanol and 1% v/v triethylamine in dichloromethane to give a white foam. (Found: C, 77.97; H, 7.33; N, 11.78. C$_{23}$H$_{25}$N$_3$+0.6 H$_2$O requires C, 77.98; H, 7.45; N, 11.86%); δ (d$_6$-DMSO, 360 MHz) 1.7–1.8 (4H, m, CH$_2$'s), 2.0–2.1 (2H, m, CH$_2$), 2.7–2.8 (3H, m, CH$_2$+CH), 2.9–3.0 (4H, m, CH$_2$'s), 3.49 (2H, s, ARCH$_2$), 7.0–7.7 (9H, m, ArH), 12.4 (1H, br s, NH); m/z (CI$^+$, NH$_3$) 344 (M$^+$+H).

EXAMPLES 5 AND 6

3-(1-(2-Phenylethyl)-4-piperidinyl)-4,5-dihydronaphth [2,1-d]isoxazole and 3-(1-(2-Phenylethyl)-4-piperdinyl)-4,5-dihyronaphth [1,2-c]isoxazole 2-(4-(1-(2-Phenylethyl))piperidinocarbonyl)-3,4-dihydro-1-hydroxy naphthalene (320 mg), hydroxylamine hydrochloride (278 mg) and triethylamine (560 µl) were stirred at 60° C. in methanol (3 ml) and dimethylformamide (3 ml) under nitrogen for 5 h. Water (30 ml) was added, the mixture extracted with ethyl acetate (3×25 ml), and the combined organic extracts washed with water and brine, dried (MgSO$_4$), and evaporated in vacuo. The residue was dissolved in dichloromethane (5 ml), cooled to 0° C., and triethylamine (140 µl) and methanesulphonyl chloride (78 µl) added. After 1h ethyl acetate (40 ml) was added and the mixture washed with water and brine, dried (MgSO$_4$), evaporated in vacuo, and purified by preparative thin layer chromatography, eluting with methanol (3% v/v) and triethylamine (1% v/v) in dichloromethane to give one of the isomers (68 mg) as white plates, m.p. 86°–87° C. (from ethanol): δ (360 MHz, d$_6$-DMSO) 1.7–1.8 (2H, m, NCH$_2$CH$_A$H$_B$CH), 1.90 (2H, d, J 11, NCH$_2$CH$_A$H$_B$CH), 2.10 (2H, t, J 12, CH$_2$), 2.5–2.6 (2H, m, CH$_2$), 2.7–2.8 (4H, m, CH$_2$'s), 2.8–2.9 (3H, m, CH$_2$ and CH), 3.01 (2H, d, J 12, NCH$_A$H$_B$CH$_2$CH), 7.1–7.4 (8H, m, ArH), 7.77 (1H, d, J 7.3, ArH o to isoxazole); m/z (CI$^+$, NH$_3$) 359 (M$^+$+H); and the other isomer (188 mg) as white plates, m.p. 116°–118° C. (from ethanol): δ (d$_6$-DMSO, 360 MHz) 1.7–1.8 (2H, m, NCH$_2$CH$_A$H$_B$CH), 1.88 (2H, d, J 10, NCH$_2$CH$_A$H$_B$CH), 2.10 (2H, t, J 9, CH$_2$), 2.5–2.6 (2H, m, CH$_2$), 2.7–2.8 (5H, m, CH$_2$'s and CH), 2.95–3.05 (4H, m, CH$_2$'s), 7.1–7.6 (9H, m, ArH); m/z (CI$^+$, NH$_3$) 359 (M$^+$+H).

We claim:

1. A compound of formula I, or a pharmaceutically acceptable salt thereof or a prodrug thereof:

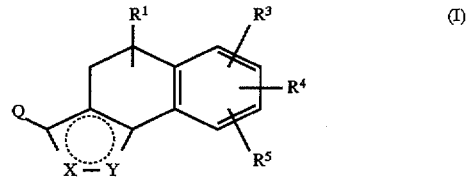

wherein the broken circle represents two non-adjacent double bonds in any position within the five-membered ring;
one of X and Y represents nitrogen, and the other of X and Y represents oxygen, sulphur or N—R$^2$;
Q represents a ring of formula Qa to Qe

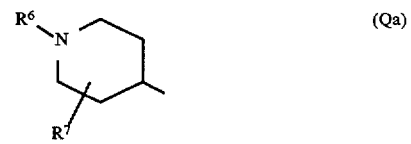

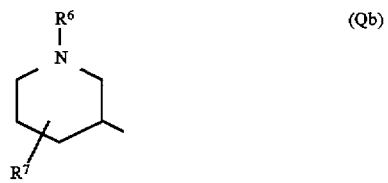

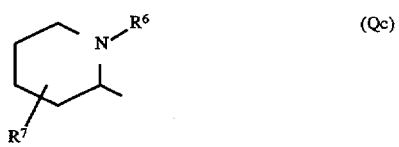

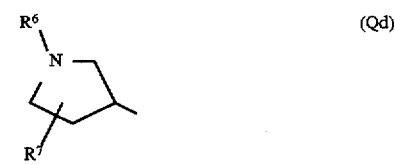

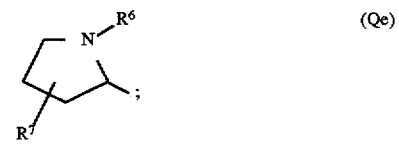

R$^1$ and R$^2$ independently represent hydrogen or C$_{1-6}$ alkyl;
R$^3$, R$^4$ and R$^5$ independently represent hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl (C$_{1-6}$)alkyl, aryl(C$_{2-6}$)alkenyl, aryl(C$_{2-6}$)alkynyl, C$_{3-7}$ heterocycloalkyl, C$_{3-7}$ heterocycloalkyl(C$_{1-6}$)alkyl, heteroaryl or heteroaryl(C$_{1-6}$)alkyl wherein the heterocycloalkyl and heteroaryl groups contain one or two heteroatoms selected from O, N or S;

$R^a$ and $R^b$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl,($C_{2-6}$) alkenyl, aryl($C_{2-6}$)alkynyl, $C_{3-7}$ heterocycloalkyl, $C_{3-7}$ heterocycloalkyl($C_{1-6}$)alkyl, heteroaryl or heteroaryl ($C_{1-6}$)alkyl wherein the heterocycloalkyl and heteroaryl groups containing one or two heteroatoms selected from O, N or S; and wherein one of $R^6$ and $R^7$ represents $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, $C_{3-7}$ heterocycloalkyl, $C_{3-7}$ heterocycloalkyl($C_{1-6}$)alkyl, heteroaryl or heteroaryl ($C_{1-6}$)alkyl wherein the heterocycloalkyl and heteroaryl groups contain one or two heteroatoms selected from O, N or S and the other of $R^6$ and $R^7$ represents hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$) alkyl, aryl($C_{2-6}$)alkenyl, aryl($C_{2-6}$)alkynyl, $C_{3-7}$ heterocycloalkyl, $C_{3-7}$ heterocycloalkyl($C_{1-6}$)alkyl, heteroaryl or heteroaryl($C_{1-6}$)alkyl wherein the heterocycloalkyl and heteroaryl groups contain one or two heteroatoms selected from O, N or S.

2. A compound as claimed in claim 1 represented by formula IA, and pharmaceutically-acceptable salts and prodrugs thereof:

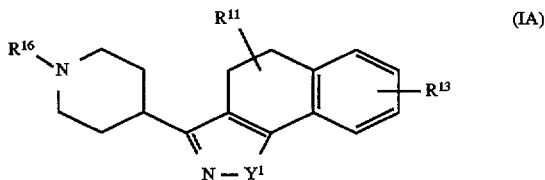

(IA)

wherein $Y^1$ represents oxygen, sulphur or N—$R^{12}$;

$R^{11}$ and $R^{12}$ independently represent hydrogen or $C_{1-6}$ alkyl;

$R^{13}$ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{16}$ represents $C_{2-6}$ alkenyl, $C_{3-7}$ cycloalkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted.

3. A compound selected from:

3-(1-benzylpiperidin-4-yl)-4,5-dihydrobenz[g]indazole;

3-[1-(2-phenylethyl)piperidin-4-yl]-4,5-dihydrobenz[g] indazole;

3-[1-(2-phenylethyl)piperidin-4-yl]-4,5-dihydronaphth[1,2-c]isoxazole;

3-[1-(2-phenylethyl)piperidin-4-yl]-4,5-dihydronaphth[2,1-d]isoxazole;

and salts and prodrugs thereof.

4. A pharmaceutical composition comprising a compound as claimed in claim 1 in association with a pharmaceutically acceptable carrier.

5. A method for treating schizophrenia which comprises administering to a patient in need of such treatment a therapeutically effective amount of a compound as claimed in claim 1.

6. A process for the preparation of a compound as claimed in claim 1 which comprises reacting a compound of formula II with a compound of formula III:

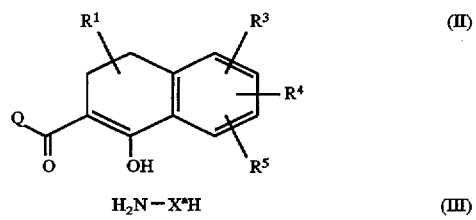

wherein Q, $R^1$, $R^3$, $R^4$ and $R^5$ are as defined in claim 1, and $X^a$ represents oxygen, sulphur or N—$R^2$ in which $R^2$ is as defined in claim 1; followed optionally, by separation of the resulting mixture of isomers; and optionally subsequently, converting a compound of formula I initially obtained into a further compound of formula I by conventional methods.

* * * * *